(12) United States Patent
Wang et al.

(10) Patent No.: US 10,568,692 B2
(45) Date of Patent: Feb. 25, 2020

(54) SURGICAL LASER TOOL

(71) Applicant: AMS Research, LLC, Minnetonka, MN (US)

(72) Inventors: Hui Wang, Fremont, CA (US); Wen-Jui Ray Chia, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 60 days.

(21) Appl. No.: 14/440,204

(22) PCT Filed: Nov. 7, 2013

(86) PCT No.: PCT/US2013/068878
§ 371 (c)(1),
(2) Date: May 1, 2015

(87) PCT Pub. No.: WO2014/074678
PCT Pub. Date: May 15, 2014

(65) Prior Publication Data
US 2015/0272679 A1 Oct. 1, 2015

Related U.S. Application Data

(60) Provisional application No. 61/724,349, filed on Nov. 9, 2012.

(51) Int. Cl.
*A61B 18/24* (2006.01)
*A61B 5/00* (2006.01)
*A61B 17/00* (2006.01)

(52) U.S. Cl.
CPC ............ *A61B 18/24* (2013.01); *A61B 5/0075* (2013.01); *A61B 5/0084* (2013.01); *A61B 2017/00057* (2013.01)

(58) Field of Classification Search
CPC ..... A61B 18/24; A61B 5/0075; A61B 5/0084; A61B 2017/00057
(Continued)

(56) References Cited

U.S. PATENT DOCUMENTS

| 5,104,392 A | 4/1992 | Kittrell et al. |
| 5,290,275 A | 3/1994 | Kittrell et al. |

(Continued)

FOREIGN PATENT DOCUMENTS

| CN | 101155545 A | 4/2008 |
| CN | 101389264 A | 3/2009 |

(Continued)

OTHER PUBLICATIONS

International Search Report and Written Opinion of PCT/US2013/068878, dated Jan. 31, 2014.

(Continued)

*Primary Examiner* — Carl H Layno
*Assistant Examiner* — Dacheng Xie
(74) *Attorney, Agent, or Firm* — Bookoff McAndrews, PLLC

(57) ABSTRACT

A surgical laser tool for performing a laser procedure at a treatment site is provided. The surgical laser tool includes a laser source, a fiber catheter, and an analytical device. The laser source is configured to generate laser energy. The fiber catheter is configured to (i) acquire optical feedback from the treatment site and (ii) deliver the laser energy to the treatment site. The analytical device is configured to analyze reflected light from the treatment site in order to allow a physician to perform a diagnosis on the treatment site.

19 Claims, 3 Drawing Sheets

(58) Field of Classification Search
USPC .................................... 606/2–19; 607/88–92
See application file for complete search history.

(56) References Cited

U.S. PATENT DOCUMENTS

| | | | |
|---|---|---|---|
| 2002/0045811 A1 | 4/2002 | Kittrell et al. | |
| 2003/0045780 A1* | 3/2003 | Utsui | A61B 1/00167 600/182 |
| 2004/0092830 A1* | 5/2004 | Scott | A61B 5/0066 600/478 |
| 2005/0251116 A1* | 11/2005 | Steinke | A61B 5/0066 606/8 |
| 2008/0002927 A1 | 1/2008 | Furnish | |
| 2008/0243031 A1* | 10/2008 | Seibel | A61B 1/0008 600/566 |
| 2011/0028790 A1* | 2/2011 | Farr | A61B 1/00052 348/77 |
| 2011/0118592 A1* | 5/2011 | Sobe | A61B 17/3207 600/424 |
| 2014/0031800 A1* | 1/2014 | Ben Oren | A61B 17/320016 606/7 |

FOREIGN PATENT DOCUMENTS

| | | |
|---|---|---|
| JP | 2007-209536 A | 8/2007 |
| JP | 4642653 B2 | 3/2011 |
| WO | 90/00035 A1 | 1/1990 |
| WO | 93/03672 A1 | 3/1993 |
| WO | 2014074678 A1 | 5/2014 |

OTHER PUBLICATIONS

EPO Communication from European Patent Application No. 13795101.8, dated Jul. 7, 2015.

* cited by examiner

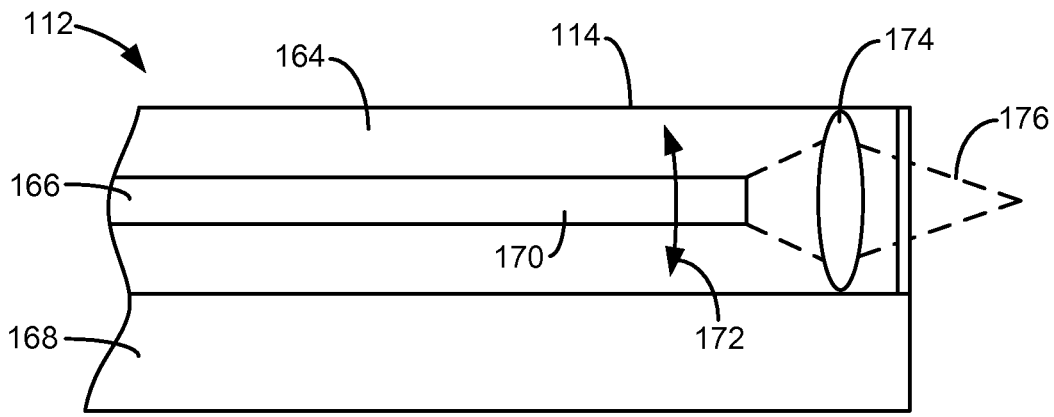
FIG. 4
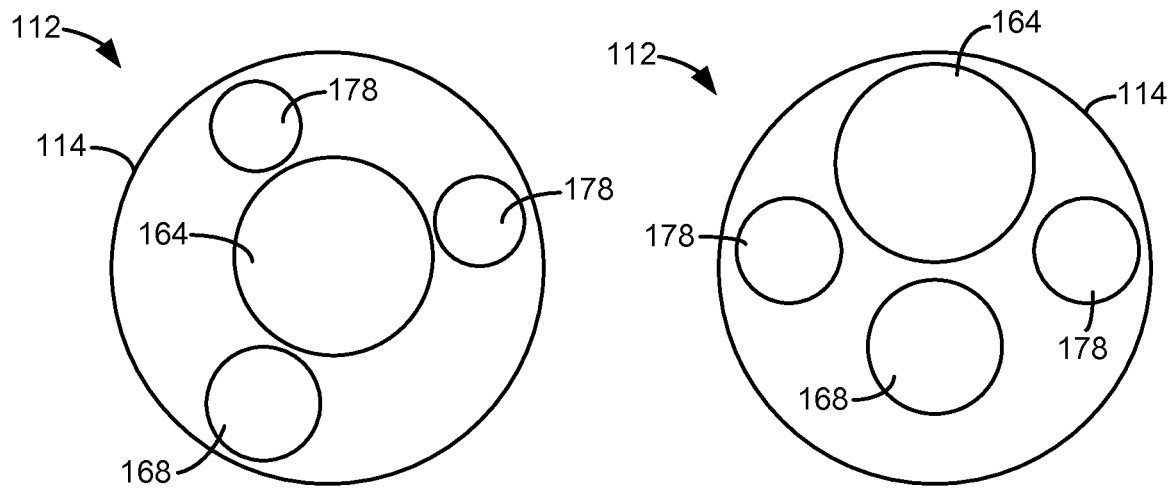
FIG. 5
FIG. 6
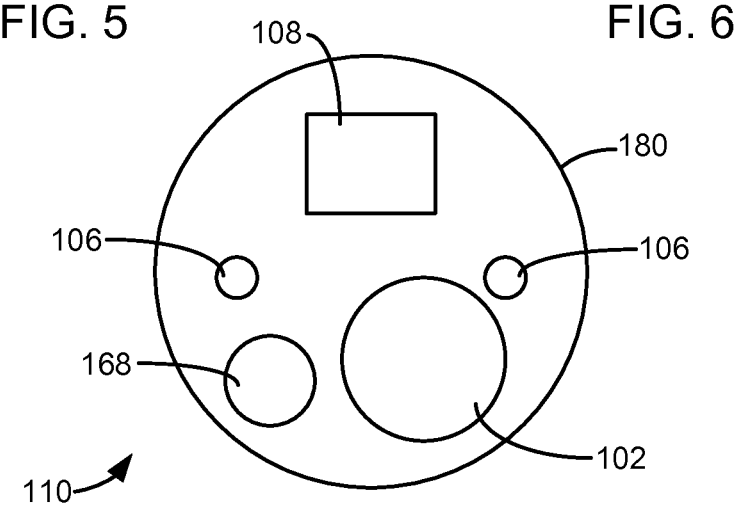
FIG. 7

SURGICAL LASER TOOL

CROSS-REFERENCE TO RELATED APPLICATION

This Application is a Section 371 National Stage Application of International Application No. PCT/US2013/068878, filed Nov. 7, 2013 and published as WO 2014/074678 A1 on May 15, 2014, in English, which claims the benefit of U.S. Provisional Application Ser. No. 61/724,349, filed Nov. 9, 2012 under 35 U.S.C. § 119(e), the contents of which are hereby incorporated by reference in their entirety.

BACKGROUND

Laser surgery can be an alternative to traditional surgical tools, as it can reduce bleeding, pain and infection. Patients after laser surgery often have less hospitalization time. In addition, a surgical laser delivered through a fiber can be easily integrated with a compact and flexible endoscopy. However, laser surgery relies on tissue vaporization or chip off. After surgery, it is very difficult to collect enough tissue samples for further histopathological analysis, which is currently considered as the golden standard for final diagnosis of many diseases, for example, cancer. Due to this reason, laser surgery is still not widely employed in many clinics.

SUMMARY

Embodiments of the invention are directed to a surgical laser tools for performing a laser procedure at a treatment site and methods of diagnosing and treating a treatment site in a patient using a surgical laser tool. Some embodiments of the surgical laser tool include a laser source, a fiber catheter, and an analytical device. The laser source is configured to generate laser energy. The fiber catheter is configured to (i) acquire optical feedback from the treatment site and (ii) deliver the laser energy to the treatment site. The analytical device is configured to analyze reflected light from the treatment site in order to allow a physician to perform a diagnosis on the treatment site.

Other embodiments of the surgical laser tool include a surgical laser, a fiber catheter, an imaging light source, an optical device, and an analytical device. The surgical laser is configured to generate laser energy. The fiber catheter includes a fiber bundle configured to image the treatment site and discharge the laser energy to the treatment site. The optical device couples light generated by the imaging light source and laser energy generated by the surgical laser to the fiber bundle. The analytical device is configured to analyze reflected light from the treatment site.

In accordance with some embodiments of the method, a surgical laser tool is provided. In some embodiments the surgical laser tool includes a laser source, a fiber catheter, a diagnostic light source, or/and an analytical device. The laser source is configured to generate laser energy. The fiber catheter is configured to (i) acquire optical feedback from the treatment site and (ii) deliver the laser energy to the treatment site. The diagnostic light source is configured to deliver light to the fiber catheter through an optical path. The analytical device is configured to analyze reflected light from the treatment site in order to allow a physician to perform a diagnosis on the treatment site. Also in the method, light from the diagnostic light source is discharged through a distal end of the fiber catheter onto the treatment site. Collected light from the diagnostic light source reflected off the treatment site is then delivered through the fiber catheter to the analytical device for analysis. A surgical laser treatment is then performed based on an analysis of the collected light.

In some embodiments, the diagnostic light source is a white light, an LED light, a pulsed laser, a continuous wave laser, or a broad band light source.

BRIEF DESCRIPTION OF THE DRAWINGS

FIG. 4 is a simplified diagram of a fiber catheter in accordance with embodiments of the invention.

FIGS. 5 and 6 are simplified cross-sectional views of a fiber catheter in accordance with embodiments of the invention.

FIG. 7 is a simplified end view of a surgical laser tool in accordance with embodiments of the invention.

DETAILED DESCRIPTION OF ILLUSTRATIVE EMBODIMENTS

Figure 1:
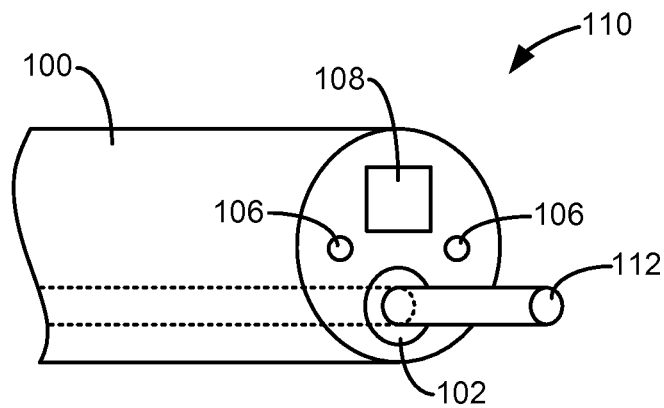
FIG. 1 is a simplified diagram of a distal end of an endoscope and a fiber catheter in accordance with embodiments of the invention.

Embodiments of the invention are described more fully hereinafter with reference to the accompanying drawings. Elements that are identified using the same or similar reference characters refer to the same or similar elements. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

Specific details are given in the following description to provide a thorough understanding of the embodiments. However, it is understood by those of ordinary skill in the art that the embodiments may be practiced without these specific details. For example, circuits, systems, networks, processes, frames, supports, connectors, motors, processors, and other components may not be shown, or shown in block diagram form in order to not obscure the embodiments in unnecessary detail.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, the present invention may be embodied as methods, systems, and/or computer program products. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code embodied in the medium. Any suitable computer readable medium may be utilized including hard disks, CD-ROMs, optical storage devices, or magnetic storage devices. Such computer readable media and memory for computer programs and software do not include transitory waves or signals.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the invention may also be described using flowchart illustrations and block diagrams. Although a flowchart may describe the operations as a sequential process, many of the operations can be performed in parallel or concurrently. In addition, the order of the operations may be re-arranged. A process is terminated when its operations are completed, but could have additional steps not included in a figure or described herein.

It is understood that one or more of the blocks (of the flowcharts and block diagrams) may be implemented by computer program instructions. These program instructions may be provided to a processor circuit, such as a microprocessor, microcontroller or other processor, which executes the instructions to implement the functions specified in the block or blocks through a series of operational steps to be performed by the processor(s) and corresponding hardware components.

Embodiments of the invention are directed to surgical laser tools, systems and surgical laser treatments. In some embodiments, the tools facilitate in vivo diagnosis through optical parameters measurement or imaging during laser surgery. Surgeons can be effectively guided to find out the resection margin and may not need to spare tissue for further histopathological analysis. More importantly, in vivo diagnostic feedbacks will enable complete and fine surgery at once, which will significantly reduce the recurrent diseases and avoid repeat surgeries.

FIG. 1 is a simplified diagram of a distal end of a conventional endoscope 100. The endoscope 100 may include a working channel or lumen 102, light outputs 106 through which light may be discharged to illuminate a treatment site, and an imaging component 108 (e.g., a CCD camera) that may be used to capture images of the treatment site.

Figure 2:
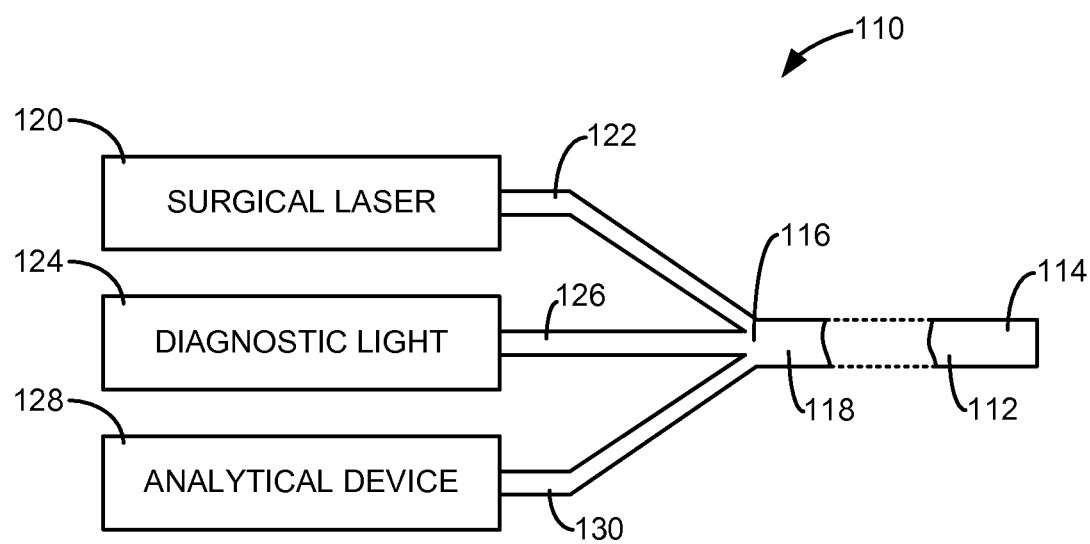
FIGS. 2 and 3 are simplified diagrams of a surgical laser tool in accordance with embodiments of the invention.

FIG. 2 is a simplified diagram of a surgical laser tool 110 in accordance with embodiments of the invention. In one embodiment, the tool 110 comprises a fiber catheter 112 (single mode or multi-mode), which may be delivered to a targeted treatment site through the working channel 102 of an endoscope or cystoscope, as illustrated in FIG. 1. In some embodiments, the fiber catheter 112 includes at least one optical fiber that is configured to acquire optical parameter feedbacks. In some embodiments the fiber catheter 112 is configured to deliver laser energy to the treatment site for a surgical laser treatment (e.g., tissue cutting, ablating, vaporization, etc.). The distal end 114 of the fiber catheter 112 may be configured to discharge laser energy along a central axis of the catheter 112 (i.e., end-fire), laterally to the central axis (i.e., side-fire), or in another conventional manner.

In some embodiments, the tool 110 includes one or more optical components 116 (e.g., fiber coupler or a beam splitter cube with free space coupling) at a proximal end 118 of the fiber catheter 112 that are configured to optically couple the at least one optical fiber of the fiber catheter 112 to multiple optical paths (122, 126, 130), each of which may be coupled to a different device.

In one embodiment, the tool 110 includes a surgical laser 120 configured to generate laser energy for use in a surgical laser treatment. The surgical laser 120 may comprise a conventional laser resonator or other device configured to generate laser energy used in laser surgical procedures, such as tissue cutting, ablating, coagulation or vaporizing procedures. The laser energy generated by the surgical laser 120 is delivered to the fiber catheter 112 through an optical path 122 and the optical components 116. The laser energy may be discharged through the distal end 114 of the fiber catheter 112 to the targeted treatment site, as mentioned above.

In one embodiment, the tool 110 includes a diagnostic light source (DLS) 124, which is configured to deliver light to the fiber catheter 112 through an optical path 126 and the optical components 116, as shown in FIG. 2. The DLS 124 can be, for example, white light, LED, pulsed or continuous waver lasers, or a broad band light source. The light from the DLS 124 can be discharged through the distal end 114 of the fiber catheter 112. In some embodiments, the DLS 124 generates broadband light using a white light, an LED, a super-luminescent LED, a laser source, or other suitable source. The DLS 124 may also include a filter to produce light having a narrow wavelength band. In some embodiments, the surgical laser 120 can also be used as the diagnostic light source.

In one embodiment, the tool 110 includes an analytical device (AD) 128, which is configured to analyze reflected light from the treatment site for diagnostics. The AD 128 can be, for example, a spectrometer, a photodetector, or a photomultiplier tube. In one embodiment, AD 128 is optically coupled to the fiber catheter 112 through an optical path 130 and the optical components 116, as shown in FIG. 2. Light, generated by the DLS 124 and discharged through the fiber catheter 112 or light from the outputs 106, is reflected from tissue in the treatment site and delivered to the AD 128 through the fiber catheter 112. In one embodiment, the AD 128 includes a spectrometer. In one embodiment, the AD 128 includes a photodetector or photo multiplier tube, which could be used, for example, for fluorescence and Raman detection.

Figure 3:
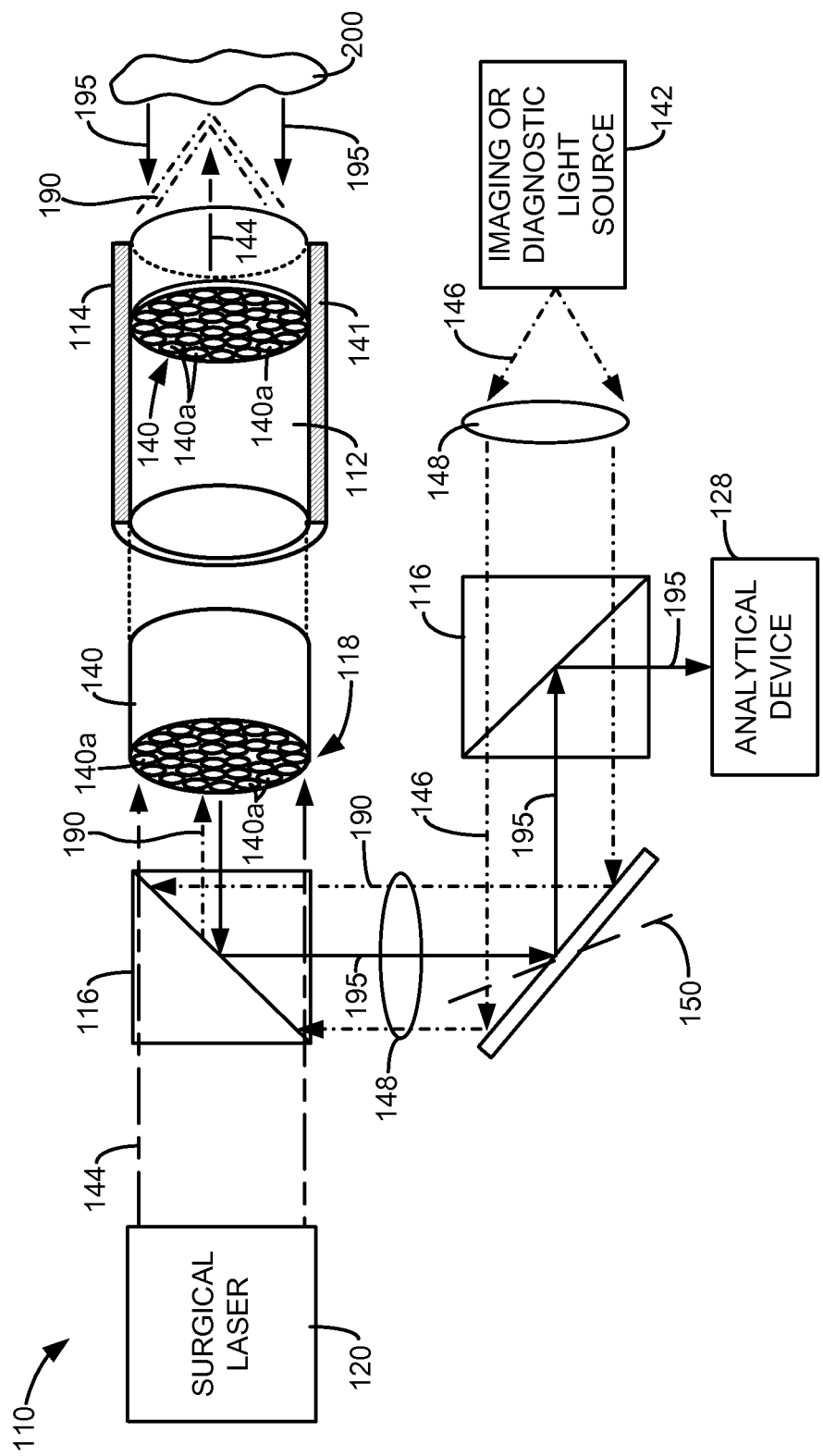

FIG. 3 is a simplified diagram of a surgical laser tool 110 in accordance with embodiments of the invention. In one embodiment, the tool 110 comprises a fiber catheter 112 comprising a fiber bundle 140 that is configured for both imaging and surgery. In one embodiment, the fiber bundle 140 is flexible and composed of a plurality of thin optical fibers 140*a*. In one embodiment, a housing 141 surrounds the fiber bundle 140. In one embodiment, the tool 110 includes a surgical laser 120, such as that described above. In one embodiment, the tool 110 includes an imaging or diagnostic light source 142.

The light generated by the imaging or diagnostic light source 142 and the laser energy generated by the surgical laser 120 are coupled to the fiber bundle 140 though a suitable optical component or components 116, such as, for example, a beam combiner, that is either polarization or non-polarization sensitive and which may be supported by the housing 141 at the proximal end 118 of the fiber bundle 140. In some embodiments, the laser energy 144 generated by the surgical laser 120 and/or the light 146 generated by the light source 142 may be optically processed using one or more lenses 148 or other optical components as necessary.

In one embodiment, the polarization states of the laser energy 144 and the light 146 are manipulated through polarization controllers to linear polarization states that are orthogonal to each other. In this case, they can be combined through a polarization sensitive beam splitter without light loss.

For imaging, the light 146 from the light source 142 is focused onto the proximal end 118 of the fiber bundle 140 through a scanner 150, which can provide X,Y scanning and be realized by galvanometers or a piezoelectric actuator, in accordance with some embodiments of the invention. In one embodiment, the scanning beam 190 is conducted through the fiber bundle 140 to the distal end 114 of the fiber bundle 140. The beam 190 can be further focused onto the targeted treatment site 200 through a lens or other optical component as necessary.

The reflected light 195 from the targeted treatment site 200 is collected by fiber bundle 140 and fed back through the fiber bundle 140 to the AD 128, such as, for example, a spectrometer, a photodetector or photo multiplier tube, or other analytical device for analysis. A beam splitter 116, which may be dichromatic, polarization sensitive, or polarization non-sensitive, may be used to direct the reflected light 195 to the AD 128, as shown in FIG. 3.

In one embodiment, the light 195 fed back through the fiber bundle 140 can be further processed based on the signal from each location during the scanning to form an image. During surgery, surgeons can initiate laser surgery based on the acquired images. Different imaging schemes could be employed here. For example, for optical coherence tomography, the light source 142 could be a broadband light source (i.e. superluminescent LED or swept light source); for nonlinear optical imaging (i.e. Raman, two photon), the light source 142 could be a pulsed laser; for fluorescence imaging, the light source could be a narrow band light from a laser or filtered from a broad band light source, as mentioned above. The fiber bundle 140 can be further simplified to a multi-mode or a single mode fiber. However, the optical signal such as Raman scattering and fluorescence can still be acquired.

FIG. 4 is a simplified illustration of a fiber catheter 112 in accordance with other embodiments of the invention that can be used to simultaneously image, diagnose and perform laser surgery of a target treatment site 200. In one embodiment, the fiber catheter 112 comprises two channels: an imaging channel 164 that receives an imaging fiber 166, and a laser channel 168 that includes an optical fiber or receives a laser fiber (not shown) for discharging surgical laser energy to the target site. In one embodiment, the fiber catheter 112 includes a magnetic force or a piezoelectric actuator that moves or vibrates the distal end 170 of the imaging fiber 166, as indicated by arrow 172, for scanning purposes. A lens or other optical component 174 may be used to focus light 176 to, or from, the imaging fiber 166. Exemplary imaging modalities that could be realized in this scheme and others described herein include optical coherence topography (OCT), two photon microscopy, fluorescence lifetime imaging, fluorescence confocal imaging, Raman scattering imaging, reflection confocal imaging, coherent anti-stock imaging, and second harmonic imaging.

As mentioned above, the laser channel 168 is used to accommodate a surgical laser fiber, which can discharge laser energy from a laser source to perform a surgical laser treatment at a treatment site 200, such as a tissue ablation treatment. In one embodiment, the fiber catheter 112 is used with the surgical laser tool 110 to perform the surgical laser treatment based on the observation of the optical imaging feedback through the imaging fiber 166, in accordance with embodiments described above.

In some embodiments, the fiber catheter 112 includes additional channels, as shown in the simplified cross-sectional views of the fiber catheter 112 provided in FIGS. 5 and 6. In one embodiment, the fiber catheter 112 includes one or more irrigant channels 178 for providing or removing a flow of liquid (e.g., saline) or air for cooling or cleaning the target treatment site.

In one embodiment, the surgical laser tool 110 may include a modified endoscope or cystoscope 180, a simplified end view of which is provided in FIG. 7. In one embodiment, a thin surgical laser channel 168 having, for example, a diameter of 100 um to 1 mm, is formed in the endoscope 180 for accommodating a surgical laser fiber. Also illustrated in FIG. 7 are a working channel 102 to receive, for example, a fiber or fiber catheter, light outputs 106, and an imaging component 108, which can be, for example, a CCD camera.

The optical feedback signal can also be used as a control signal to the laser, which can adjust laser parameters, such as power level, pulse width, lasing duration etc.

Embodiments of the invention combine diagnosis and treatment into a single tool. The tool may be used to eliminate lab intensive, time-consuming and delayed histological analysis. It can also be used to provide surgeons with an objective guidance for finding resection margins. More importantly, it will enable laser as a major tool for surgery, which will lead to low health cost for both patients and hospitals.

Although the present invention has been described with reference to preferred embodiments, workers skilled in the art will recognize that changes may be made in form and detail without departing from the spirit and scope of the invention.

What is claimed is:

1. A tool comprising:
   a fiber catheter including a proximal end, a distal end, and a plurality of channels extending therebetween;
   a laser source configured to generate a laser energy;

a light source configured to generate a diagnostic light;
a first fiber disposed in a first channel of the plurality of channels, the first fiber being configured to: (i) deliver the diagnostic light to a treatment site from the light source in a first direction parallel to a longitudinal axis of the fiber catheter, and (ii) receive optical feedback from a portion of the diagnostic light reflected from the treatment site;
a second fiber disposed in a second channel of the plurality of channels, the second fiber being configured to deliver the laser energy to the treatment site from the laser source in a second direction parallel to the longitudinal axis of the fiber catheter;
an actuator configured to vibrate a distal end of the first fiber within the first channel; and
an analytical device configured to analyze the optical feedback.

2. The tool of claim 1, wherein each of the first and second fibers comprises at least one optical fiber, and the actuator is responsive to one of electricity and a magnetic force.

3. The tool of claim 1, further comprising one or more optical components configured to:
couple the second fiber to the laser source;
couple the first fiber to the light source and the analytical device; and
modify the optical feedback prior to receipt by the analytical device.

4. The tool of claim 1, wherein the diagnostic light source includes one of a white light source, an LED light source, a pulsed laser source, a laser source, and a broad band light source.

5. The tool of claim 1, wherein the analytical device includes one of a spectrometer, a photodetector, and a photomultiplier tube.

6. The tool of claim 1, wherein the first channel is separate from the second channel.

7. The tool of claim 6, wherein the first fiber is vibrated independent of the second fiber.

8. The tool of claim 1, wherein the laser source is configured to generate the laser energy according to laser parameters, and the analytical device is configured to output a control signal configured to determine the laser parameters.

9. A system comprising:
the tool of claim 1, and
a scope including at least one working channel configured to deliver the distal end of the fiber catheter to the treatment site.

10. A method comprising the steps of:
positioning a distal end of a tool adjacent a treatment site, the tool comprising:
a laser source configured to generate a laser energy;
a light source configured to generate a diagnostic light;
a fiber catheter including:
a first fiber configured to: (i) deliver the diagnostic light to the treatment site in a first direction parallel to a longitudinal axis of the fiber catheter, and (ii) receive a portion of the diagnostic light reflected from the treatment site, and
a second fiber configured to deliver the laser energy to the treatment site in a second direction parallel to the longitudinal axis of the fiber catheter;
oscillating a distal end of the first fiber relative to the fiber catheter in a direction transverse to the longitudinal axis of the fiber catheter;
discharging the diagnostic light from the light source through the distal end of the first fiber onto the treatment site;
delivering, to an analytical device, optical feedback received from the portion of the diagnostic light reflected from the treatment site; and
analyzing, with the analytical device, the optical feedback.

11. The method of claim 10, wherein the light source includes one of a white light source, an LED light source, a laser source, and a broad band light source.

12. The method of claim 10, wherein the analytical device includes one of a spectrometer, a photodetector, and a photomultiplier tube.

13. A tool comprising:
a laser source configured to generate a laser energy;
an imaging light source configured to generate an imaging light;
a fiber catheter comprising:
a first channel including a first fiber configured to: (i) deliver the imaging light to a treatment site in a first direction parallel to a longitudinal axis of the fiber catheter, and (ii) receive optical feedback from a portion of the imaging light reflected from the treatment site, and
a second channel including a second fiber configured to discharge the laser energy to the treatment site in a second direction parallel to the longitudinal axis of the fiber catheter;
an actuator configured to vibrate a distal end of the first fiber independent of a distal end of the second fiber along an axis transverse to the longitudinal axis of the fiber catheter;
at least one optical device for coupling the first fiber to the imaging light and the second fiber to the laser source; and
an analytical device configured to analyze the optical feedback.

14. The tool of claim 13, wherein the first fiber comprises a plurality of optical fibers.

15. The tool of claim 13, wherein the imaging light source includes one of a broadband light source, a pulsed laser source, and a narrow band light source.

16. The tool of claim 13, wherein the analytical device includes one of a spectrometer, a photodetector, and a photomultiplier tube.

17. A method comprising the steps of:
positioning a distal end of the fiber catheter of claim 13 adjacent the treatment site;
powering the actuator to vibrate the distal end of the first fiber;
discharging the imaging light through the distal end of the first fiber onto the treatment site while the actuator is powered;
delivering the optical feedback to the analytical device through the first fiber; and
analyzing the optical feedback with the analytical device.

18. The method of claim 17, further comprising the step of processing, with a processor circuit, the optical feedback to form an image of the treatment site.

19. The method of claim 17, wherein the laser source is configured to generate the laser energy according to laser parameters, and the method further comprises the steps of:
outputting, with the analytical device, a control signal configured to determine the laser parameters; and discharging the laser energy through the second fiber according to the laser parameters.

* * * * *